(12) United States Patent
Schmidt et al.

(10) Patent No.: US 6,616,989 B1
(45) Date of Patent: Sep. 9, 2003

(54) ISOXAZOLE DERIVATIVES, AND THEIR USE IN LIQUID-CRYSTALLINE MIXTURES

(75) Inventors: Wolfgang Schmidt, Dreieich (DE); Barbara Hornung, Hasselroth (DE); Rainer Wingen, Hattersheim (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 09/708,853

(22) Filed: Nov. 7, 2000

(30) Foreign Application Priority Data

Nov. 9, 1999 (DE) .......................... 199 53 801

(51) Int. Cl.[7] ...................... C09K 19/34; C07D 413/04
(52) U.S. Cl. .................... 428/1.1; 252/299.61; 548/247
(58) Field of Search ........................ 252/299.61, 299.01; 428/1.1; 548/247

(56) References Cited

U.S. PATENT DOCUMENTS 6,231,786 B1 * 5/2001 Wingen et al. ........ 252/299.61

FOREIGN PATENT DOCUMENTS

| DE | 19748432 | 5/1999 |
|---|---|---|
| EP | 0032362 | 7/1981 |
| EP | 0916714 | 5/1999 |
| JP | 60-54375 | 3/1985 |
| JP | 10-333113 | 12/1998 |

OTHER PUBLICATIONS

CAPLUS 1962: 436304.*
CAPLUS 1983: 215512.*
CA 125: 155039, 1996.*
Iglesias et al, "FLC's with a Five–Membered Ring in the Mesogenic Core", Liquid Crystals, 1997, vol. 22, No. 1, pp. 37–46.
Barbera et al, "β–Diketone Pyrazole and Isoxazole Derivatives With Polar Groups: Liquid Crystalline and Non–Linear Optical Properties", Liquid Crystals, 1997, vol. 22, No. 3, pp. 265–273.
Barbera et al, "Mesogenic Behaviour in Some Pyrazole and Isoxazole Derivatives", Liquid Crystals, 1992, vol. 11, No. 6, pp. 887–897.
Sequel et al, "Synthesis and Thermotropic Properties of New Mesogenic Pyrazole and Isoxazole Derivatives", Liquid Crystals, 1992, vol. 11, No. 6, pp. 899–903.
Bartulin et al, "Synthesis and Mesomorphic Properties of 3,5–Bis–(p–n–Alkoxyphenyl) Isoxazole and 3,5–Bis–(p–n–Alkoxyphenyl) Pyrazole", Mol. Cryst. Liq. Crystal, 1993, vol. 225, pp. 175–182.
Bartulin et al, "Synthesis and Mesomorphic Properties of 3,5–Bis–Alkoxyphenyl–Pyrazoles and –Isoxazoles", Mol. Cryst. Liq. Cryst., 1992, vol. 220, pp. 67–75.

* cited by examiner

*Primary Examiner*—Shean C. Wu
(74) *Attorney, Agent, or Firm*—Frommer Lawrence & Haug LLP

(57) ABSTRACT

Isoxazole derivatives of the formula (I)

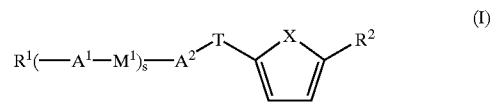

where the symbols and indices have the following meanings, for example:

T is

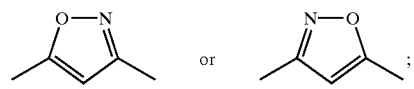

X is S or O $R^1$ and $R^2$ are identical or different and are each hydrogen, F, CN or a straight-chain or branched $C_1$–$C_{20}$-alkyl or $C_2$–$C_{20}$-alkenyl radical (with or without asymmetric carbon atoms), $A^1$ and $A^2$ are undirected and identical or different and are each phenylene-1,4-diyl, $M^1$ is undirected and is —OC(=O)—, —OCH$_2$—, —SC(=O)—, —SCH$_2$—, —CH$_2$CH$_2$—, —OC(=O)CH$_2$CH$_2$—, —OCH$_2$CH$_2$CH$_2$—, —C≡C—, —(CH$_2$)$_4$— or a single bond;

a is 0 or 1, are used in liquid-crystal mixtures.

12 Claims, No Drawings

ISOXAZOLE DERIVATIVES, AND THEIR USE IN LIQUID-CRYSTALLINE MIXTURES

BACKGROUND OF THE INVENTION (1) Field of the Invention

Besides nematic and cholesteric liquid crystals, optically active, tilted, smectic (ferroelectric) liquid crystals have also recently been used in commercial display devices.

(2) Description of Related Art

Clark and Lagerwall have been able to show that the use of ferroelectric liquid crystals (FLCs) in very thin cells results in opto-electrical switching or display elements which have response times which are faster by a factor of up to 1000 compared with conventional TN ("twisted nematic") cells (see, for example, EP-A 0 032 362). Owing to this and other favorable properties, for example the possibility of bistable switching and the virtually viewing angle-independent contrast, FLCs are basically highly suitable for areas of application such as computer displays.

For a more detailed explanation of the technical requirements of FLCs, reference is made to European Patent Application 0 916 714 and DE-A 197 48 432.

Liquid-crystalline 3,5-diphenylisoxazoles have been described in JP 60-054375, Liq. Cryst. 1997, 22, 3746, and Liq. Cryst. 1997, 22, 265–273. The synthesis and mesogenic properties of symmetrically substituted bisalkoxy-3,5-diphenylisoxazoles has been described in Liq. Cryst. 1992, 11, 887–897, Liq. Cryst. 1992, 11, 899, Mol. Cryst. Liq. Cryst. 1992, 220, 67–75, and Mol. Cryst. Liq. Cryst. 1993, 225, 175–182. JP-A 10-333113 describes 3,5-diphenylisoxazoles for use in ferroelectric liquid-crystal mixtures.

However, since the development, in particular of ferroelectric liquid-crystal mixtures, can in no way be regarded as complete, display manufacturers are interested in a wide variety of components for mixtures, partly because only the interaction of the liquid-crystalline mixtures with the individual components of the display device or of the cells (for example the alignment layer) allows conclusions to be drawn on the quality of the liquid-crystalline mixtures too.

BRIEF SUMMARY OF THE INVENTION

It has now been found that isoxazole derivatives of the formula (I) below, in which the isoxazole moiety is linked in position 3 and/or 5 to a thiophene or furan moiety, even when admixed in small amounts, have a favorable effect on the properties of liquid-crystal mixtures, in particular chiral smectic mixtures, for example regarding the dielectric anisotropy and/or the melting point, but also regarding the switching behavior, the tilt angle value and the temperature dependence of the tilt angle.

DETAILED DESCRIPTION OF THE INVENTION

The invention therefore provides isoxazole derivatives of the formula (I)

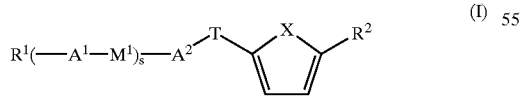

(I)

where the symbols and indices have the following meanings:

T is

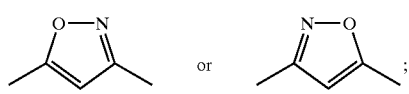

or

X is S or O $R^1$ and $R^2$ are identical or different and are each hydrogen, F, CN or a straight-chain or branched $C_1$–$C_{20}$-alkyl or $C_2$–$C_{20}$-alkenyl radical (with or without asymmetric carbon atoms), where a) one to three nonterminal $CH_2$ groups may be replaced, independently of one another, by —O—, —S— or —C(=O)—, with the proviso that heteroatoms cannot be linked directly to one another, and/or b) one CH2 group may be replaced by —CH=CH— or —C≡C—, and/or c) one CH2 group may be replaced by —Si(CH3)2-, cyclopropane-1,2-diyl, oxirane-2,3-diyl, cyclobutane-1,3-diyl, cyclopentane-1,4-diyl, bicyclo[1.1.1]pentane-1,3-diyl or cyclohexane-1,4-diyl, and/or d) one or more H atoms may be replaced, independently of one another, by F or CN, e) in the case of an alkyl or alkenyl radical containing asymmetric carbon atoms, the asymmetric carbon atoms have —CH3, —OCH3, —CF3, —F, —CN and/or —Cl as substituents, with the proviso that only one of R1 and R2 can be hydrogen, F or CN;

$A^1$ and $A^2$ are undirected and identical or different and are each phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced, independently of one another, by CN, $CH_3$ or F, 1-cyclohexene-1,4-diyl, in which one H atom may be replaced by F, pyridine-2,5-diyl, unsubstituted or monosubstituted by F, thiophene-2,5-diyl, unsubstituted or monosubstituted by F; furan-2,5-diyl or naphthalene-2,6-diyl, unsubstituted or monosubstituted or disubstituted by CN or F;

$M^1$ is undirected and is —OC(=O)—, —OCH$_2$—, —SC(=O)—, —SCH$_2$—, —CH$_2$CH$_2$—, —OC(=O)CH$_2$CH$_2$—, —OCH$_2$CH$_2$CH$_2$—, —C≡C—, —(CH$_2$)$_4$— or a single bond;

a is 0 or 1.

The symbols and indices in the formula (I) preferably have the following meanings:

$R^1$ and $R^2$ are preferably identical or different and are each hydrogen or a straight-chain or branched $C_1$–$C_{18}$-alkyl or $C_2$–$C_{18}$-alkenyl radical (with or without asymmetric carbon atoms), where a) one or two nonterminal CH2 groups may be replaced, independently of one another, by —O— or —C(=O)—, with the proviso that heteroatoms cannot be linked directly to one another, and/or b) one or more H atoms may be replaced by F, c) in the case of an alkyl or alkenyl radical containing asymmetric carbon atoms, the asymmetric carbon atoms have —CH3, —CF3 and or —F as substituents, with the proviso that only one of R1 and R2 can be hydrogen.

$A^1$ and $A^2$ are preferably undirected and identical or different and are each phenylene-1,4-diyl, unsubstituted or monosubstituted or disubstituted by F, cyclohexane-1,4-diyl, 1-cyclohexene-1,4-diyl, pyridine-2,5-diyl, unsubstituted or monosubstituted by F, or thiophene-2,5-diyl.

$M^1$ is preferably undirected and is —OC(=O)—, —OCH$_2$— or a single bond.

a is preferably 0.

Particular preference is given to the following compounds of the formulae (I-1) to (I-12).

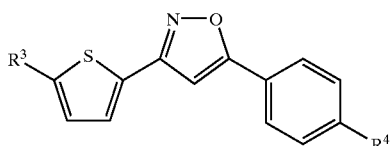
(I-1)

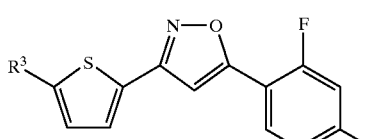
(I-2)

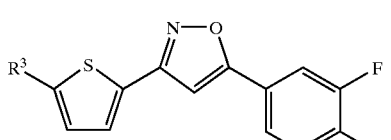
(I-3)

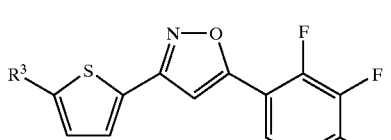
(I-4)

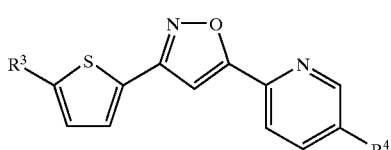
(I-5)

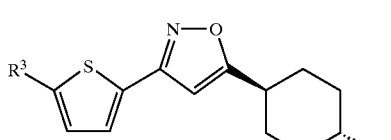
(I-6)

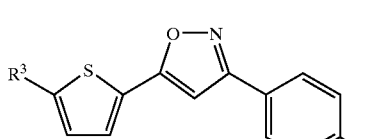
(I-7)

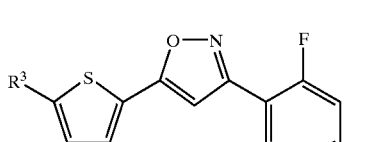
(I-8)

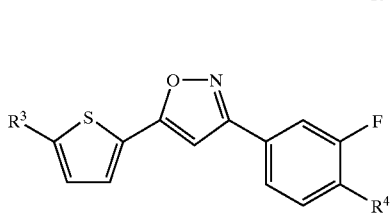
(I-9)

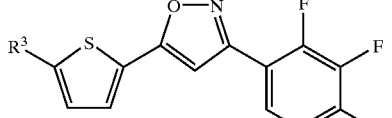
(I-10)

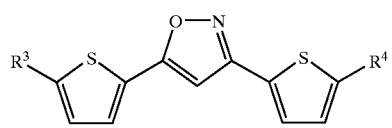
(I-11)

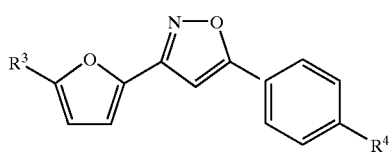
(I-12)

in which:

$R^3$ is hydrogen or a straight-chain or branched $C_1$–$C_{15}$-alkyl or $C_2$–$C_{15}$-alkenyl or $C_1$–$C_{15}$-alkyloxy radical (with or without asymmetric carbon atoms), $R^4$ is hydrogen or a straight-chain or branched $C_1$–$C_{15}$-alkyl or $C_2$–$C_{15}$-alkenyl radical (with or without asymmetric carbon atoms), in which one nonterminal $CH_2$ group may also be replaced by —O— and in which one or more H atoms may be replaced by F, with the proviso that only one of $R^3$ and $R^4$ can be hydrogen.

Particular preference is given to compounds of the formula (I), in particular (I-1) to (I-12), in which $R^3$ is a straight-chain $C_1$–$C_{15}$-alkyl or $C_2$–$C_{15}$-alkenyl radical and $R^4$ is a straight-chain alkyl or alkyloxy radical having 1 to 15 carbon atoms.

"Undirected" means that incorporation of the group in the form of its mirror image is possible.

"Terminal" means, for example in $R^1$, the $CH_2$ groups connected to H.

Of the compounds of the formula (I) which are to be used as optically active components (dopants), preference is given to those in which the alkyl group contains the asymmetric carbon atoms in the form of at least one of the following groups:

a) —C*H(CH$_3$)C$_m$H$_{2m+1}$, where m has a value of from 2 to 8 b) —OC*H(CH$_3$)C$_m$H$_{2m+1}$, where m has a value of from 2 to 8 c) —OC*H(CH$_3$)CO$_2$C$_m$H$_{2m+1}$, where m has a value of from 1 to 10 d) —OC(=O)C*H(CH$_3$)OC$_m$H$_{2m+1}$, where m has a value of from 1 to 10 e) —OC(=O)C*H(F)C$_m$H$_{2m+1}$, where m has a value of from 1 to 10 f) —OCH$_2$C*H(F)C$_m$H$_{2m+1}$, where m has a value of from 1 to 10 g) —OCH$_2$C*H(F)C*H(F)C$_m$H$_{2m+1}$, where m has a value of from 1 to 10 h) oxirane-2,3-diyl in which C* denotes the asymmetric carbon atom.

The compounds according to the invention are prepared by methods known per se from the literature, as described in standard works on organic synthesis, for example Houben-Weyl, Methoden der organischen Chemie [Methods of Organic Chemistry], Georg-Thieme-Verlag, Stuttgart.

However, it may prove necessary to vary or modify the literature methods for the requirements of mesogenic units, since, for example, functional derivatives having long (>$C_6$) alkyl chains tend to be less reactive than, for example, the methyl or ethyl analogues.

Particular reference is made in this connection to the following synthesis schemes, in which the synthesis of the isoxazole derivatives of the invention, in which the isoxazole moiety is linked in position 3 and/or 5 to a thiophene moiety, is illustrated in more detail by way of example.

Scheme 1

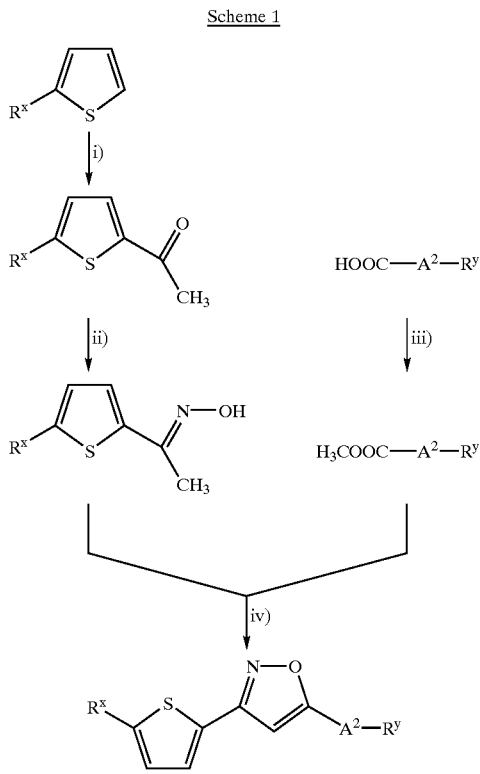

i) $CH_3COCl/AlCl_3/CH_2Cl_2$; ii) $H_2NOH.HCl/EtOH/NEt_3$; iii) 1. $SOCl_2/DMF$; 2. $MeOH/NEt_3/DMAP$; iv) 1.2 equiv. n-BuLi/THF/n-hexane; 2. $HCl/H_2O$ (as described in J. Org. Chem. 1970, 35, 1806–1810)

Scheme 2

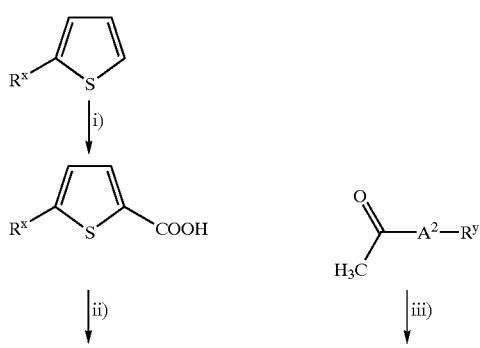

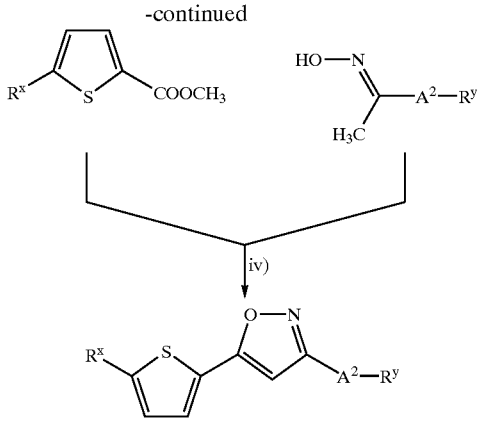

i) n-BuLi/THF/n-hexane; 2. $CO_2$; ii) 1. $SOCl_2/DMF$; 2. $MeOH/NEt_3/DMAP$; iii) $H_2NOH.HCl/EtOH/NEt_3$; iv) 1.2 equiv. n-BuLi/THF/n-hexane; 2. $HCl/H_2O$ (as described in J. Org. Chem. 1970, 35, 1806–1810)

The group $R^x$ is identical to $R^2$ or a suitable precursor thereof (protected or unprotected) which can be converted into this group in subsequent steps by methods known per se and customary to the person skilled in the art.

The group $R^y$ is identical to $R^1$ or $(M^1-A^1-)_aR^1$ or a suitable precursor thereof (protected or unprotected) which can be converted into this group in subsequent steps by methods known per se and customary to the person skilled in the art.

The 2- or 5-substituted thiophenes, thiophene-2-carboxylic acids and thiophene-2-carboxylates shown in the schemes can be obtained, for example, in accordance with the procedures described in EP-A 0 392 510, J. Chem. Soc. Perkin Trans. I, 791, Eur. J. Med. Chem. 1989, 24, 65, Org. Synth. 1946, Vol. III, 2639, Heterocycles 1995, 41, 13, J. Org. Chem. 1980, 45, 4528.

The isoxazole derivatives of the invention, in which the isoxazole moiety is linked in position 3 and/or 5 to a furan moiety, are prepared in a similar manner. The corresponding 2- or 5-substituted furans, furan-2-carboxylic acids and furan-2-carboxylates can likewise be prepared in a similar manner and are described, for example, in J. Chem. Soc. Perkin Trans. I, 791, Org. Synth. 1946, Vol. 111, 2639 and DE-A-199 41 649.

As far as the linking of functional derivatives or precursors of the isoxazoles of the invention with other liquid-crystal-specific units is concerned, express reference is made to DE-A 197 48 432, which gives a list of methods customary to the person skilled in the art.

The invention further provides the use of compounds of the formula (I) in liquid-crystal mixtures, preferably smectic and nematic liquid-crystal mixtures, particularly preferably chiral smectic liquid-crystal mixtures. Particular preference is given to the use in chiral smectic liquid-crystal mixtures operated in switching and display devices having active matrix elements. Particular preference is likewise given to the use in chiral smectic (ferroelectric) liquid-crystal mixtures operated in inverse mode.

Very particular preference is given to the use in mixtures for active matrix LCDs in which the chiral smectic liquid-crystal layer forms a monostable-switching monodomain.

The invention furthermore provides liquid-crystal mixtures, preferably smectic and nematic liquid-crystal mixtures, particularly preferably chiral smectic liquid-crystal mixtures, which comprise one or more compounds of the formula (I).

The liquid-crystal mixtures according to the invention generally comprise from 2 to 35 components, preferably from 2 to 25 components, particularly preferably from 2 to 20 components.

They generally comprise from 0.01 to 80% by weight, preferably from 0.1 to 60% by weight, particularly preferably from 0.1 to 30% by weight, of one or more, preferably from 1 to 10, particularly preferably from 1 to 5, very particularly preferably from 1 to 3, compounds of the formula (I) according to the invention.

Further components of liquid-crystal mixtures which comprise compounds of the formula (I) according to the invention are preferably selected from known compounds having smectic and/or nematic and/or cholesteric phases. Further mixture components which are suitable in this context are listed, in particular, in international patent application WO 97/04039 and in DE-A 197 48 432, which are incorporated herein by reference.

The mixtures according to the invention can in turn be used in electro-optical or fully optical elements, for example display elements, switching elements, light modulators, elements for image processing and/or signal processing, or generally in the area of nonlinear optics.

The invention therefore furthermore provides a switching and/or display device comprising a smectic or nematic liquid-crystal mixture, preferably a chiral smectic liquid-crystal mixture, which comprises one or more compounds of the formula (I).

Particular preference is given to chiral smectic switching and/or display devices comprising active matrix elements (cf. e.g. DE-A 19822830).

Particular preference is likewise given to chiral smectic (ferroelectric) switching and/or display devices, which are especially preferably operated in inverse mode.

The present application cites various documents, for example in order to illustrate the technical background to the invention. All these documents are incorporated herein by reference.

The examples which follow illustrate the invention further without restricting it.

EXAMPLE 1

3-(5-Butylthiophen-2-yl)-5-(4-octylphenyl)-isoxazole

Step 1

2-Butylthiophene (obtained by Friedel-Crafts acylation of thiophene with butyryl chloride followed by Wolf-Kizner reduction in accordance with EP-A 0 392 510) is acetylated with acetyl chloride in dichloromethane under $AlCl_3$ catalysis. Customary work-up followed by purification by distillation affords 2-acetyl-5-butylthiophene, b.p. 92° C./0.8 mbar.

Step 2

A solution of 2-acetyl-5-butylthiophene in ethanol is heated to the boil together with equimolar amounts of hydroxylamine hydrochloride and triethylamine. Customary work-up followed by purification of the raw product by recrystallization from ethanol affords the corresponding oxime as colorless crystals.

Step 3

4-Octylbenzoyl chloride (obtained by reacting 4-octylbenzoic acid with thionyl chloride) is esterified with methanol in the presence of an equimolar amount of triethylamine and 0.1 mol % of DMAP. Customary work-up followed by purification by distillation affords methyl 4-octylbenzoate as a colorless liquid, b.p. 112° C./0.25 mbar.

Step 4

The 1-(5-butylthiophen-2-yl)-ethanone oxime obtained in step 2 is dissolved in tetrahydrofuran under an inert gas atmosphere and doubly deprotonated with 2 equivalents of n-butyllithium at 0° C. The solution is admixed with a solution of 0.5 equivalents of methyl 4-octylbenzoate in tetrahydrofuran, and the mixture is stirred for 30 min at 0° C., then admixed with 3 M HCl and refluxed for 1 h. Customary work-up followed by purification by column chromatography over silica gel 60 (eluent: dichloromethane/heptane 1:1) and recrystallizsation affords 3-(5-butylthiophen-2-yl)-5-(4-octylphenyl)-isoxazole; X 63 $S_C$ 82 $S_A$ 88 N 89 I.

EXAMPLE 2

3-(5-Butylthiophen-2-yl)-5-4-octyloxyphenyl)-isoxazole is prepared similar to Example 1, but using methyl 4-octyloxybenzoate instead of methyl 4-octylbenzoate, affording 3-(5-butylthiophen-2-yl)-5-(octyloxyphenyl)-isoxazole; X 72 $S_C$ 119 $S_A$ 119 N 122.2 I.

EXAMPLE 3

5-(2,3-difluoro-4-nonylphenyl)-3-(5-pentylthiophen-2-yl)-isoxazole is prepared similar to Example 1, but using 2-pentylthiophene instead of 2-butylthiophene and methyl 2,3-difluoro-4-nonylbenzoate instead of methyl 4-octylbenzoate.

EXAMPLE 4

3-(5-Butylthiophen-2-yl)-5-(trans-4-heptylcyclohexyl)-isoxazole is prepared similar to Example 1, but using methyl trans-4-heptylcyclohexanecarboxylate instead of methyl 4-octylbenzoate.

EXAMPLE 5

3-(5-Heptylthiophen-2-yl)-5-(6-hexyloxypyridin-3-yl)-isoxazole is prepared similar to Example 1, but using 2-heptylthiophene instead of 2-butylthiophene and methyl 6-hexaloxypyridine-3-carboxylate instead of methyl 4-octylbenzoate.

EXAMPLE 6

4-[3-(5-Butylthiophen-2-yl)-isoxazol-5-yl]-phenyl nonanoate is prepared similar to Example 1, but using methyl 4-(tetrahydropyran-2-yloxy)benzoate (obtained by reacting methyl 4-hydroxybenzoate with 3,4-dihydro-2H-pyran and 4-toluenesulfonic acid in dichloromethane) instead of methyl 4-octylbenzoate, affording 4-[3-(5-butylthiophen-2-yl)-isoxazol-5-yl]-phenol. DCC esterification (Angew. Chem. 1978, 90, 556) with pelargonic acid affords 4-[3-(5-butylthiophen-2-yl)-isoxazol-5-yl]-phenyl nonanoate.

EXAMPLE 7

3-(5-Butylthiophen-2-yl)-5-{4-[(S)-2-fluorodecyloxy]-phenyl}-isoxazole is prepared similar to Example 6, but 3-(5-butylthiophen-2-yl)-5-(4-hydroxyphenyl)-isoxazole is etherified with (S)-2-fluoro-1-decanol by the method of Mitsunobu (diethyl azodicarboxylate/triphenylphosphine in tetrahydrofuran; Synthesis 1981, 1).

EXAMPLE 8

5-(5-Butylthiophen-2-yl)-3-(4-octylphenyl)-isoxazole

Octylbenzene is acetylated with acetyl chloride in dichloromethane under $AlCl_3$ catalysis and the resulting 4-octylacetophenone is converted into the corresponding oxime with hydroxylamine hydrochloride in ethanol/triethylamine. The oxime is dissolved in tetrahydrofuran under an inert gas atmosphere and doubly deprotonated with 2 equivalents of n-butyllithium. The solution is admixed with 0.5 equivalents of methyl 5-butyl-2-thiophenecarboxylate (obtained from 2-butylthiophene by lithiating with n-butyllithium in THF and reacting with carbon dioxide followed by esterification with methanol) and allowed to warm up to room temperature. Customary work-up followed by purification by recrystallization affords 5-(5-butylthiophen-2-yl)-3-(4-octylphenyl)-isoxazole; X 60 N 56 I.

EXAMPLE 9

3-(5-Butylthiophen-2-yl)-5-(5-heptylthlophen-2-yl)-isoxazole is prepared similar to Example 1, but using methyl 5-heptyl-2-thiophenecarboxylate (obtained from 2-heptylthiophene by lithiating with n-butyllithium in THF and reacting with carbon dioxide followed by esterification with methanol) instead of methyl 4-octylbenzoate.

The following compounds (Examples 10 to 52) are prepared similar to Examples 1 to 9

EXAMPLE 10
5-(4-Heptylphenyl)-3-(5-pentylthiophen-2-yl)-isoxazole

EXAMPLE 11
5-(4-Octylphenyl)-3-(5-pentylthiophen-2-yl)-isoxazole

EXAMPLE 12
5-(4-Hexylphenyl)-3-(5-pentylthiophen-2-yl)-isoxazole

EXAMPLE 13
5-(4-Nonylphenyl)-3-(5-pentylthiophen-2-yl)-isoxazole

EXAMPLE 14
5-(4-Decylphenyl)-3-(5-pentylthiophen-2-yl)-isoxazole

EXAMPLE 15
3-(5-Butylthiophen-2-yl)-5-(4-heptylphenyl)-isoxazole

EXAMPLE 16
3-(5-Butylthiophen-2-yl)-5-(4-hexylphenyl)-isoxazole

EXAMPLE 17
3-(5-Butylthiophen-2-yl)-5-(4-nonylphenyl)-isoxazole

EXAMPLE 18
3-(5-Butylthiophen-2-yl)-5-(4-decylphenyl)-isoxazole

EXAMPLE 19
3-(5-Propylthiophen-2-yl)-5-(4-undecylphenyl)-isoxazole

EXAMPLE 20
3-(5-Butylthiophen-2-yl)-5-(4-pentylphenyl)-isoxazole

EXAMPLE 21
5-(4-Butylphenyl)-3-(5-heptylthiophen-2-yl)-isoxazole

EXAMPLE 22
5-(4-Decylphenyl)-3-(5-propylthiophen-2-yl)-isoxazole

EXAMPLE 23
3-(5-Heptylthiophen-2-yl)-5-(4-hexylphenyl)-isoxazole

EXAMPLE 24
3-(5-Heptylthiophen-2-yl)-5-(4-pentylphenyl)-isoxazole

EXAMPLE 25
3-(5-Heptylthiophen-2-yl)-5-(4-octylphenyl)-isoxazole

EXAMPLE 26
3-(5-Heptylthiophen-2-yl)-5-(4-nonylphenyl)-isoxazole

EXAMPLE 27
5-(4-Nonylphenyl)-3-(5-propylthiophen-2-yl)-isoxazole

EXAMPLE 28
5-(4-Heptylphenyl)-3-(5-hexylthiophen-2-yl)-isoxazole

EXAMPLE 29
3-(5-Hexylthiophen-2-yl)-5-(4-octylphenyl)-isoxazole

EXAMPLE 30
3-(5-Hexylthiophen-2-yl)-5-(4-nonylphenyl)-isoxazole

EXAMPLE 31
3-(5-Hexylthiophen-2-yl)-5-(4-pentylphenyl)-isoxazole

EXAMPLE 32
5-(4-Heptylphenyl)-3-(5-heptylthiophen-2-yl)-isoxazole

EXAMPLE 33
3-(5-Decylthiophen-2-yl)-5-(4-propylphenyl)-isoxazole

EXAMPLE 34
3-(5-Butylthiophen-2-yl)-5-(4'-pentylbiphenyl-4-yl)-isoxazole

EXAMPLE 35
5-(4-Octylphenyl)-3-(5-pent-1-enylthiophen-2-yl)-isoxazole

EXAMPLE 36
4-[3-(5-Butylthiophen-2-yl)-isoxazol-5-yl]-phenyl trans-4-pentylcyclohexanecarboxylate

EXAMPLE 37
5-{4-[4-(Butyldimethylsilanyl)-butoxy]-phenyl}-3-(5-butylthiophen-2-yl)-isoxazole

EXAMPLE 38
3-(4-Octyloxyphenyl)-5-(5-pent-1-enylthiophen-2-yl)-isoxazole

EXAMPLE 39
3-(5-Butylthiophen-2-yl)-5-(5-nonylthiophen-2-yl)-isoxazole

EXAMPLE 40
3-(5-Heptylthiophen-2-yl)-5-(5-propylthiophen-2-yl)-isoxazole

EXAMPLE 41
3-(5-Heptylthiophen-2-yl)-5-(5-pentylthiophen-2-yl)-isoxazole

EXAMPLE 42
3-(5-Heptylthiophen-2-yl)-5-(5-nonylthiophen-2-yl)-isoxazole

EXAMPLE 43
3-(5-Decylthiophen-2-yl)-5-(5-pentylthiophen-2-yl)-isoxazole

EXAMPLE 44
3-(5-Heptylthiophen-2-yl)-5-[4-(trans-4-pentylcyclohexyl)-phenyl]-isoxazole

EXAMPLE 45
5-(5-Butylthiophen-2-yl)-3-(4-octyloxyphenyl)-isoxazole

EXAMPLE 46
5-(4-Nonylphenyl)-3-thiophen-2-yl-isoxazole

EXAMPLE 47

5-(4-Fluorophenyl)-3-(5-heptylthiophen-2-yl)-isoxazole

EXAMPLE 48

3-(5-Heptylthiophen-2-yl)-5-(3,4,5-trifluorophenyl)-isoxazole

EXAMPLE 49

5-(5-Ethylfuran-2-yl)-3-(4-octyloxyphenyl)-isoxazole

EXAMPLE 50

3-(5-Ethyifuran-2-yl)-5-(4-octylphenyl)-isoxazole

EXAMPLE 51

5-(5-Ethylfuran-2-yl)-3-(5-heptylthiophen-2-yl)-isoxazole

EXAMPLE 52

3-Furan-2-yl-5-(4-nonylphenyl)-isoxazole

What is claimed is:
1. An isoxazole derivative of the formula (I)

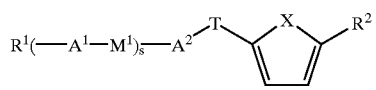 (I)

where the symbols and indices have the following meanings:
T is

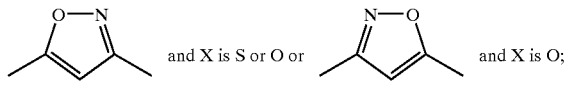

$R^1$ and $R^2$ are identical or different and are each hydrogen, F, CN or a straight-chain or branched $C_1$–$C_{20}$-alkyl or $C_2$–$C_{20}$-alkenyl radical (with or without asymmetric carbon atoms), where
   a) one to three nonterminal $CH_2$ groups may be replaced, independently of one another, by —O—, or —C(=O)—, with the proviso that heteroatoms cannot be linked directly to one another; and/or
   b) one $CH_2$ group may be replaced by —CH=CH— or —C≡C—; and/or
   c) one $CH_2$ group may be replaced by —Si(CH$_3$)$_2$—, cyclopropane-1,2-diyl, oxirane-2,3-diyl cyclobutane-1,3-diyl, cyclopentane-1,4-diyl, bicyclo[1.1.1]pentane-1,3-diyl or cyclohexane-1,4-diyl; and/or
   d) one or more H atoms may be replaced, independently of one another, by F or CN;
   e) in the case of an alkyl or alkenyl radical containing asymmetric carbon atoms, the asymmetric carbon atoms have —CH$_3$, —OCH$_3$, —CF$_3$, —F, —CN and/or —Cl as substituents;
   f) with the proviso that-only one of $R^1$ and $R^2$ is a hydrogen, F or CN;
$A^1$ and $A^2$ are undirected and identical or different and are each phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced, independently of one another by CN, CH$_3$ or F, 1-cyclohexene-1,4-diyl, in which one H atom may be replaced by F, pyridine-2,5-diyl, unsubstituted or monosubstituted by F, thiophene-2,5-diyl, unsubstituted or monosubstituted by F, furan-2,5-diyl or naphthalene-2,6-diyl, unsubstituted or monosubstituted or disubstituted by CN or F;

$M^1$ is undirected and is —OC(=O)—, —OCH$_2$—, —SC(=O)— —SCH$_2$— —CH$_2$CH$_2$—, —OC(=O)CH$_2$CH$_2$— —OCH$_2$CH$_2$CH$_2$—, —C≡C—, —(CH$_2$)$_4$— or a single bond;

a is 0 or 1.

2. An isoxasole derivative as claimed in claim 1, where the symbols and indices in the formula (I) have the following meanings:

T is

$R^1$ and $R^2$ are identical or different and are each hydrogen, or a straight-chain or branched $C_1$–$C_{18}$-alkyl or $C_2$–$C_{18}$-alkenyl radical (with or without asymmetric carbon atoms), where
   d) one to three nonterminal $CH_2$ groups may be replaced, independently of one another, by —O—, or —C(=O)—, with the proviso that heteroatoms cannot be linked directly to one another, and/or
   e) one or more H atoms may be replaced by F;
   f) in the case of an alkyl or alkenyl radical containing asymmetric carbon atoms, the asymmetric carbon atoms have —CH$_3$, —CF$_3$ and/or —F as substituents;
   g) with the proviso that only one of $R^1$ and $R^2$ is a hydrogen;
$A^2$ is undirected and is phenylene-1,4-diyl, unsubstituted or monosubstituted or disubstituted by F, cyclohexane-1,4-diyl, 1-cyclohexene-1,4-diyl, pyridine-2,5-diyl, unsubstituted or monosubstituted by F, or thiophene-2,5-diyl; and a is 0.

3. A liquid-crystal mixture comprising at least one isoxazole derivative as claimed in claim 1.

4. A liquid-crystal mixture as claimed in claim 3, which is chiral smectic.

5. A liquid-crystal mixture as claimed in claim 3, which is nematic.

6. A liquid-crystal mixture as claimed in claim 3, which comprises from 0.01 to 80% by weight of one or more compounds of the formula (I).

7. A switching and/or display device, which comprises a liquid-crystal mixture as claimed in claim 3.

8. A switching and/or display device as claimed in claim 7, which comprises active matrix elements and wherein the liquid-crystal layer forms a monostable-switching monodomain.

9. A switching and/or display device as claimed in claim 7, wherein the liquid-crystal mixture is chiral smectic.

10. A switching and display device as claimed in claim 9, which is operated in inverse mode.

11. An isoxazole derivative of the formula (I)

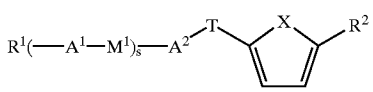 (I)

where the symbols and indices have the following meanings:

T is

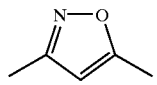

X is S $R^1$ and $R^2$ are identical or different and are each hydrogen, F, CN or a straight-chain or branched $C_1$–$C_{20}$-alkyl or $C_2$–$C_{20}$-alkenyl radical (with or without asymmetric carbon atoms), where (a) one to three nonterminal $CH_2$ groups may be replaced, independently of one another, by —S— or —C(=O)—, with the proviso that heteroatoms cannot be linked directly to one another; or (b) one $CH_2$ group may be replaced by —CH=CH— or —C≡C—; and/or (c) one $CH_2$ group may be replaced by —Si($CH_3$)$_2$—, cyclopropane-1,2-diyl, oxirane-2,3-diyl cyclobutane-1,3-diyl, cyclopentane-1,4-diyl, bicyclo[1.1.1]pentane-1,3-diyl or cyclohexane-1,4-diyl; and/or (d) one or more H atoms may be replaced, independently of one another, by F or CN;

(e) in the case of an alkyl or alkenyl radical containing asymmetric carbon atoms, the asymmetric carbon atoms have —$CH_3$, —$OCH_3$, —$CF_3$, —F, —CN and/or —Cl as substituents;

(f) with the proviso that only one of $R^1$ and $R^2$— is a hydrogen, F or CN;

$A^1$ and $A^2$ are undirected and identical or different and are each phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced, independently of one another, by CN, $CH_3$ or F; 1-cyclohexene-1,4-diyl, in which one H atom may be replaced by F, pyridine-2,5-diyl, unsubstituted or monosubstituted by F, thiophene-2,5-diyl, unsubstituted or monosubstituted by F; furan-2,5-diyl or naphthalene-2,6-diyl, unsubstituted or monosubstituted or disubstituted by CN or F;

$M^1$ is undirected and is —OC(=O)—, $OCH_2$—, —SC(=O)—, —$SCH_2$—, —$CH_2CH_2$—, —OC(=O)$CH_2CH_2$—, —$OCH_2CH_2CH_2$—, —C≡C—, —($CH_2$)$_4$— or a single bond; and a is 0 or 1.

12. An isoxazole derivative as claimed in claim 11 where the symbols and indices in the formula (I) have the following meanings:

T is

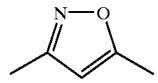

X is S $R^1$ and $R^2$ are identical or different and are each hydrogen or a straight-chain or branched $C_1$–$C_{18}$-alkyl or $C_2$–$C_{18}$-alkenyl radical (with or without asymmetric carbon atoms), where, in d) one or two nonterminal $CH_2$ groups may be replaced, independently of one another, by —C(=O)— with the proviso that heteroatoms cannot be linked directly to one another; and/or in e) one or more H atoms may be replaced by F;

in f) in the case of an alkyl or alkenyl radical containing asymmetric carbon atoms, the asymmetric carbon atoms have —$CH_3$, —$CF_3$ and or —F as substituents;

in g) with the proviso that only one of $R^1$ and $R^2$ is a hydrogen;

$A^2$ is undirected and is phenylene-1,4-diyl, unsubstituted or monosubstituted or disubstituted by F, cyclohexane-1,4-diyl; 1-cyclohexene-1,4-diyl, pyridine-2 5-diyl, unsubstituted or monosubstituted by F, or thiophene-2,5-diyl; and a is 0.

* * * * *